US012583909B2

(12) United States Patent
Kim et al.

(10) Patent No.: US 12,583,909 B2
(45) Date of Patent: Mar. 24, 2026

(54) METHOD OF PRODUCING ADM COLLAGEN FIBER, ADM COLLAGEN FIBER PRODUCED USING METHOD, AND APPARATUS FOR PRODUCING ADM COLLAGEN FIBER

(71) Applicants: GENEWEL CO., LTD., Seongnam-si (KR); UNIVERSITY-INDUSTRY COOPERATION GROUP OF KYUNG HEE UNIVERSITY, Yongin-si (KR)

(72) Inventors: Hong Doo Kim, Yongin-si (KR); Mohamad Shamim Reza, Suwon-si (KR); Hye Ri Lee, Daejeon (KR); Mi Ran Cho, Yongin-si (KR); Jun Ho Kim, Gwangju-si (KR)

(73) Assignees: GENEWEL CO., LTD., Seongnam-si (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 790 days.

(21) Appl. No.: 17/792,608

(22) PCT Filed: Jan. 8, 2021

(86) PCT No.: PCT/KR2021/000253
§ 371 (c)(1),
(2) Date: Jul. 13, 2022

(87) PCT Pub. No.: WO2021/145610
PCT Pub. Date: Jul. 22, 2021

(65) Prior Publication Data
US 2023/0033537 A1 Feb. 2, 2023

(30) Foreign Application Priority Data
Jan. 14, 2020 (KR) ........................ 10-2020-0004913

(51) Int. Cl.
*C07K 14/78* (2006.01)
*D01D 5/06* (2006.01)
*D01D 5/10* (2006.01)
*D01D 10/06* (2006.01)

(52) U.S. Cl.
CPC .............. *C07K 14/78* (2013.01); *D01D 5/10* (2013.01); *D01D 10/06* (2013.01); *D10B 2211/06* (2013.01)

(58) Field of Classification Search
CPC . C07K 14/78; D01D 5/10; D01D 5/06; D01D 10/06; D10B 2211/06; D01F 2/02
See application file for complete search history.

(56) References Cited

U.S. PATENT DOCUMENTS 5,911,942 A * 6/1999 Fofonoff ............... D06M 15/15
427/601
2012/0273993 A1* 11/2012 Shoseyov ................. D01F 4/00
530/356

FOREIGN PATENT DOCUMENTS

| CN | 108977912 A | 12/2018 |
|---|---|---|
| JP | 2005314865 A | 11/2005 |
| JP | 2006342472 A | 12/2006 |
| KR | 10-2001-0090876 A | 10/2001 |
| KR | 10-2018-0028229 A | 3/2018 |

OTHER PUBLICATIONS

Suh, et al. "One Stage Allogenic Acellular Dermal Matrices (ADM) and Split-Thickness Skin Graft with Negative Pressure Wound Therapy." Skin Grafts, edited by Madhuri Gore, InTech., 2013, Chapter 4, pp. 35-50. (Year: 2013).*
Ahmad et al. Effect of 1-ethyl-3-(3-dimethylaminopropyl) carbodiimide and N-hydroxysuccinimide concentrations on the mechanical and biological characteristics of cross-linked collagen fibres for tendon repair. Regen Biomater 2(2): 77-85, 2015.*
Chen et al. Process development of an acellular dermal matrix (ADM) for biomedical applications. Biomaterials 25: 2679-2686, 2004.*
Ehrmann et al. The growth of cells of a transparent gel of reconstituted rat-tail collagen. J National Cancer Institute 16(6): 1375-1403, 1956.*
English translation of entire JP 2005314865; published Nov. 10, 2005.*
English translation of entire JP 2006342472; published Dec. 21, 2006.*
English translation of entire CN108977912; published Dec. 11, 2018.*
Fosnot et al. Acellular Dermal Matrix: General Principles for the Plastic Surgeon. Asthetic Surg J 31(7S): 5S-12S, 2011.*
Harris et al. In vitro fibrillogenesis of collagen type I in varying ionic and pH conditions. Micron 49: 60-68, 2013.*
Li et al. pH effects on collagen fibrillogenesis in vitro: Electrostatic interactions and phosphate binding. Materials Sci Eng C 29: 1643-1649, 2009.*

(Continued)

*Primary Examiner* — Bridget E Bunner
(74) *Attorney, Agent, or Firm* — SZDC Law PC

(57) ABSTRACT
The present invention relates to a method of producing an ADM collagen fiber, an ADM collagen fiber produced using the method, and an apparatus for producing the ADM collagen fiber. More particularly, the present invention relates to a method of producing an ADM collagen fiber including a step of extruding an acidic ADM collagen solution into a basic solution to form filaments. The present invention has an effect of providing a method of producing an ADM collagen fiber, an ADM collagen fiber produced using the method, and an apparatus for producing the ADM collagen fiber. According to the present invention, since a collagen solution raw material having a required concentration may be prepared by immediately pulverizing ADM collagen shells, economic efficiency and productivity may be increased through reduction in production cost and time. In addition, mass production is possible by using a continuous process apparatus with a simple structure.

8 Claims, 3 Drawing Sheets

(56) References Cited

OTHER PUBLICATIONS

Wakuda et al. Native collagen hydrogel nanofibres with anisotropic structure using core-shell electrospinning. Sci Reports 8: 6248, 2018.*

Zeugolis et al. Post-self-assembly experimentation on extruded collagen fibres for tissue engineering applications. Acta Biomaterialia 4: 1646-1656, 2008.*

* cited by examiner

[FIG. 1]
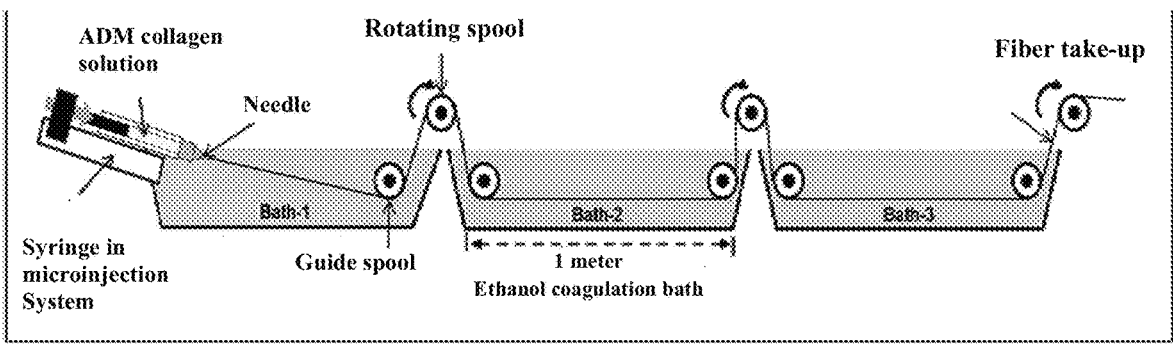
[FIG. 2]
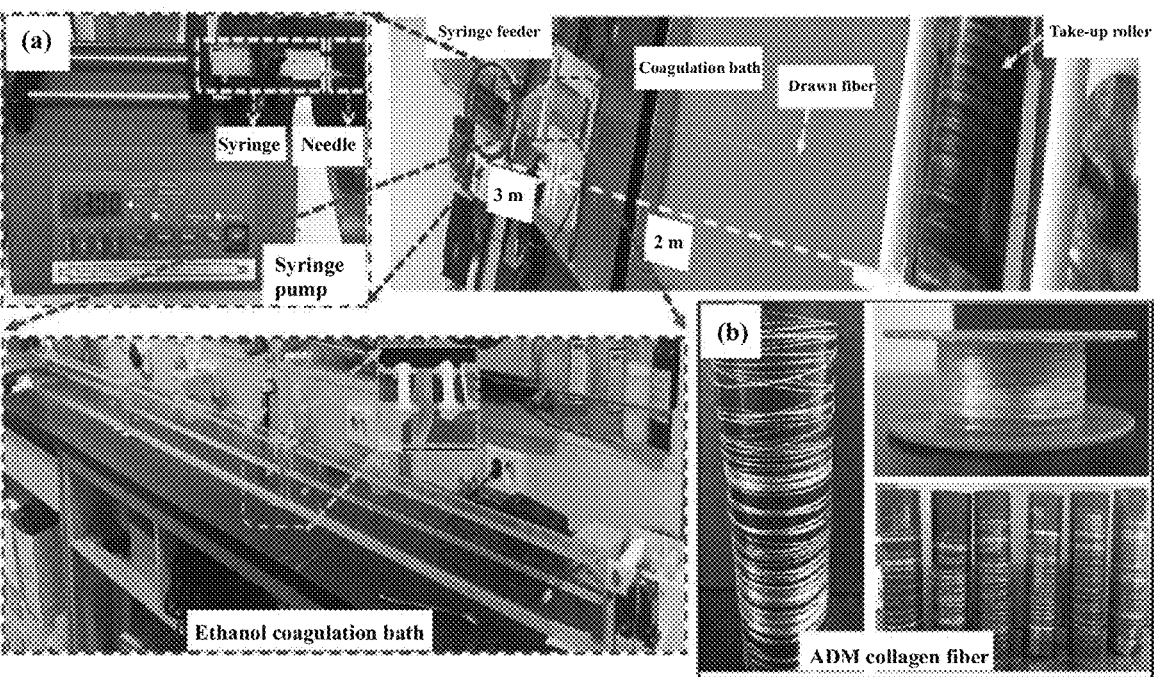

[FIG. 3]
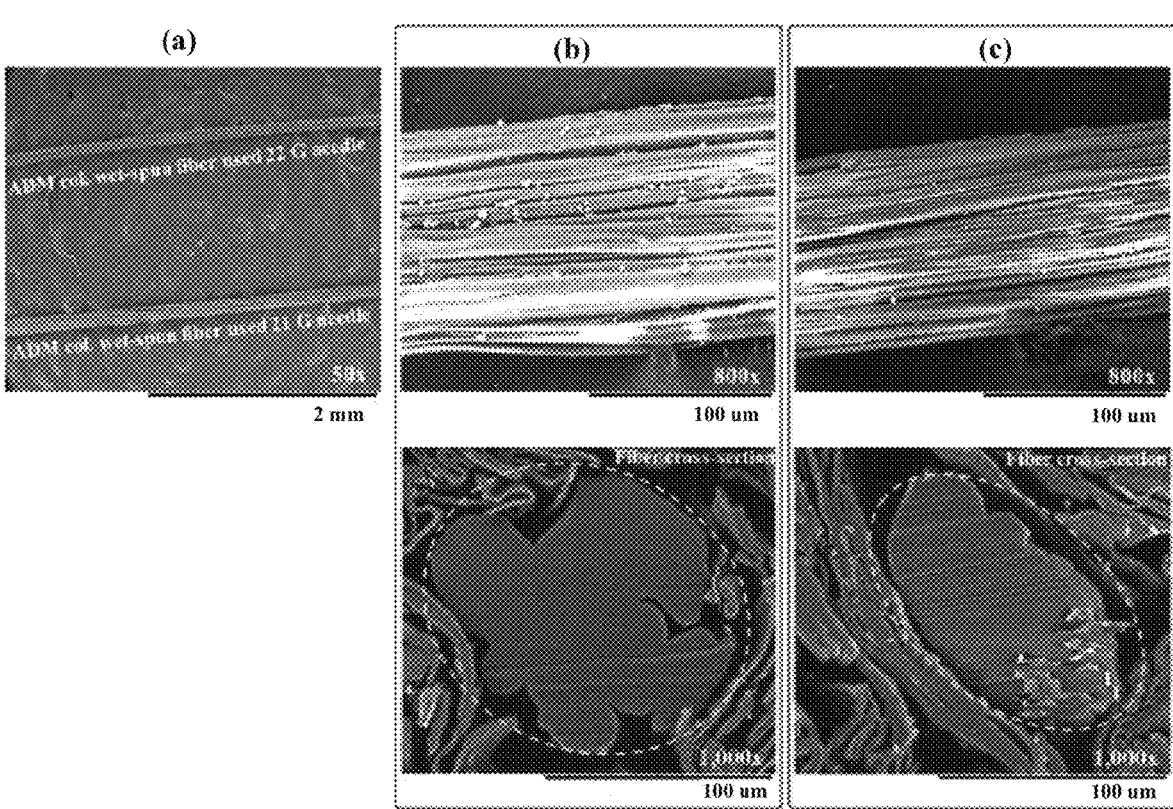

[FIG. 4]
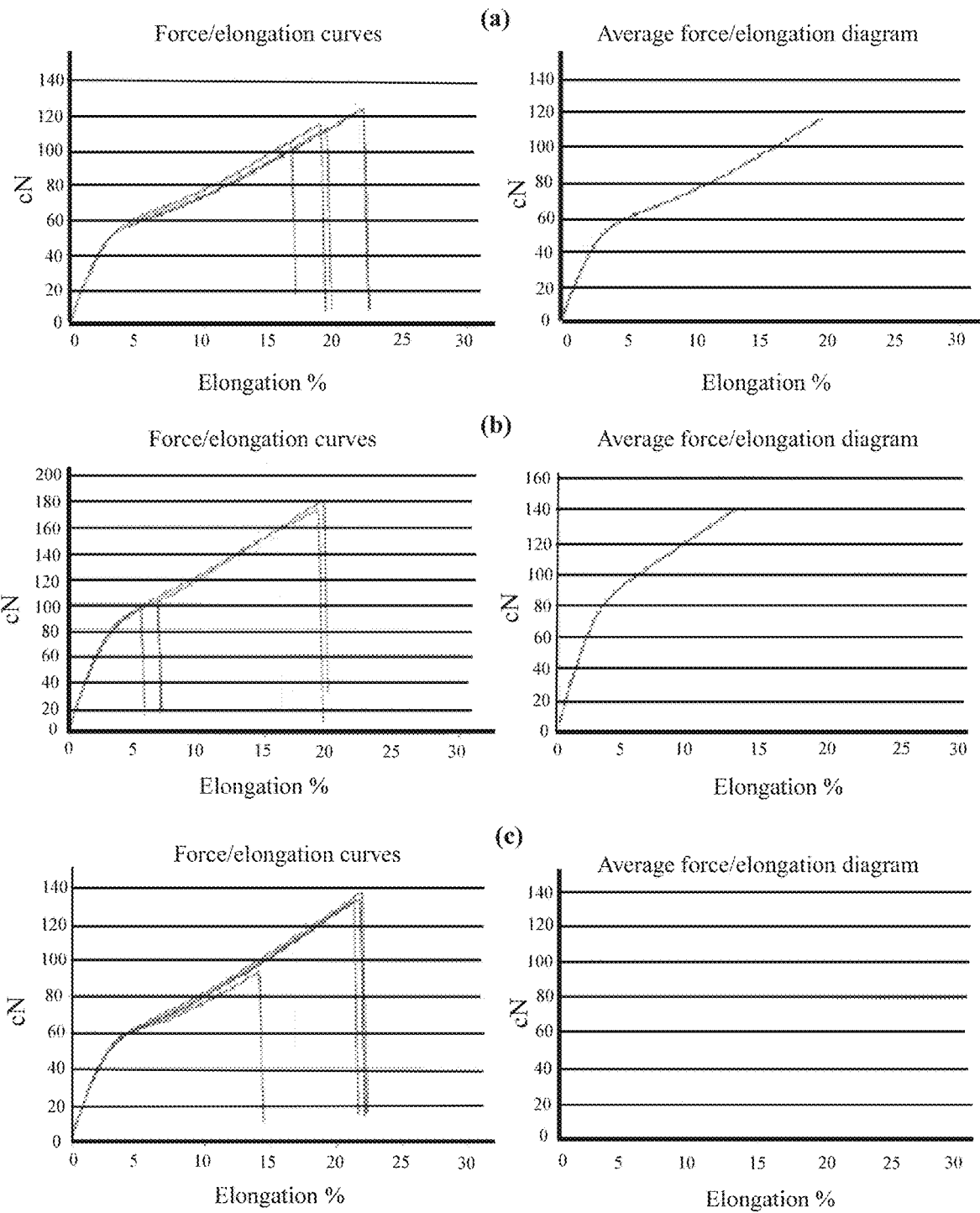

METHOD OF PRODUCING ADM COLLAGEN FIBER, ADM COLLAGEN FIBER PRODUCED USING METHOD, AND APPARATUS FOR PRODUCING ADM COLLAGEN FIBER

This application Stage Application of PCT/KR2021/000253, filed on Jan. 8, 2021, which claims priority to Korean Patent Application No. KR 10-2020-0004913, filed on Jan. 14, 2020, which is incorporated by reference for all purposes as if fully set forth herein.

TECHNICAL FIELD

The present invention relates to a method of producing an ADM collagen fiber, an ADM collagen fiber produced using the method, and an apparatus for producing the ADM collagen fiber. More particularly, the present invention relates to a method of producing an ADM collagen fiber, the method having excellent economic efficiency and productivity through reduction in production cost and time by preparing a collagen solution raw material having a required concentration by immediately pulverizing ADM collagen shells, being capable of mass production using a continuous process apparatus with a simple structure, having high efficacy due to a wide range of concentrations of available collagen solution raw materials, and being capable of producing collagen fibers having various thicknesses or properties; an ADM collagen fiber produced using the method; and an apparatus for producing the ADM collagen fiber.

Background Art

Collagen is a kind of fibrous solid and is a structural protein constituting the living tissues of various multicellular animals. At the molecular level, collagen is made up of more than 1,000 amino acids and has the shape of long, thin strips. Most of commercially available collagen is heterologous collagen extracted from the tissues of animals such as fish, pigs, and cattle. Depending on the use, atelo-collagen obtained by removing telopeptide using an enzyme may be used.

Collagen is a biodegradable and biocompatible material and is widely used as medical materials such as wound dressing materials, tissue repair materials, skin graft materials, bone graft materials, and cell culture materials.

In addition, when the skin lacks collagen or the skin ages, the skin loses elasticity and gloss due to atrophy of the subcutaneous muscle, and spots, wrinkles, age spots, and the like occur. Lack of collagen in the bones weakens the bones and increases incidence of osteoporosis, arthritis, joint pain, edema, and the like. Lack of collagen in blood vessels has been reported to cause arteriosclerosis and scurvy. For this reason, collagen is used in various applications such as health supplements, therapeutics, and cosmetics.

To use collagen for various purposes, it is necessary to process collagen extracted from natural products to obtain physical properties suitable for the use. As a conventional collagen processing method, there is a method of manufacturing a product by freeze-drying acellular dermis. However, this method has problems such as high cost and low productivity. In particular, when the freeze-dried acellular dermis is processed into powder through a post-process, the freeze-dried acellular dermis is difficult to crush. Accordingly, it is very difficult to manufacture fibers for various uses using freeze-dried acellular dermis.

Therefore, it is urgent to develop a method of producing an ADM collagen fiber, the method having high economic efficiency and productivity, having excellent efficacy due to a variety of available collagen raw materials, and being capable of producing collagen fibers having various thicknesses or properties.

DISCLOSURE

Technical Problem

Therefore, the present invention has been made in view of the above problems, and it is one object of the present invention to provide a method of producing an ADM collagen fiber, the method having excellent economic efficiency and productivity through reduction in production cost and time by preparing a collagen solution raw material having a required concentration by immediately pulverizing ADM collagen shells, being capable of mass production using a continuous process apparatus with a simple structure, having high efficacy due to a wide range of concentrations of available collagen solution raw materials, and being capable of producing collagen fibers having various thicknesses or properties; an ADM collagen fiber produced using the method; and an apparatus for producing the ADM collagen fiber.

The above and other objects can be accomplished by the present invention described below.

Technical Solution

In accordance with one aspect of the present invention, provided is a method of producing an ADM collagen fiber including a step of extruding an acidic ADM collagen solution into a basic solution to form filaments.

In accordance with another aspect of the present invention, provided is a method of producing an ADM collagen fiber including a neutralization and coagulation step of performing wet spinning of a heterogeneous acellular dermal matrix (ADM)-derived collagen solution and extruding the acidic ADM collagen solution into a basic solution to form filaments; a fiberization step of performing dehydration by treating the filaments formed in the neutralization and coagulation step with an organic solvent; a coagulation step of drying the filaments dehydrated in the fiberization step under vacuum or atmospheric pressure; and a winding step of winding the filaments dried in the coagulation step.

In accordance with still another aspect of the present invention, provided is a method of producing an ADM collagen fiber including a step of performing wet spinning of a heterogeneous acellular dermal matrix (ADM)-derived collagen solution and extruding the acidic ADM collagen solution into a basic solution having a pH of 9 to 12 to form filaments.

In accordance with still another aspect of the present invention, provided is a method of producing an ADM collagen fiber including a neutralization and coagulation step of performing wet spinning of a heterogeneous acellular dermal matrix (ADM)-derived collagen solution and extruding the acidic ADM collagen solution into a basic solution having a pH of 9 to 12 to form filaments; a fiberization step of performing dehydration by treating the filaments formed in the neutralization and coagulation step with an organic solvent; a coagulation step of drying the filaments dehydrated in the fiberization step under vacuum or atmospheric pressure; and a winding step of winding the filaments dried in the coagulation step.

In accordance with still another aspect of the present invention, provided is a method of producing an ADM collagen fiber including a step of performing wet spinning of a heterogeneous acellular dermal matrix (ADM)-derived collagen solution and extruding the acidic ADM collagen solution into a basic solution at a nozzle discharge rate of 9 to 13 ml/h to form filaments.

In accordance with still another aspect of the present invention, provided is a method of producing an ADM collagen fiber including a neutralization and coagulation step of performing wet spinning of a heterogeneous acellular dermal matrix (ADM)-derived collagen solution and extruding the acidic ADM collagen solution into a basic solution at a nozzle discharge rate of 9 to 13 ml/h to form filaments; a fiberization step of performing dehydration by treating the filaments formed in the neutralization and coagulation step with an organic solvent; a coagulation step of drying the filaments dehydrated in the fiberization step under vacuum or atmospheric pressure; and a winding step of winding the filaments dried in the coagulation step.

In accordance with still another aspect of the present invention, provided is an ADM collagen fiber produced by the method.

In accordance with still another aspect of the present invention, provided is an ADM collagen fiber including, in a cross-sectional view of a fiber, a single-layer structure or a double-layer structure with different outer and inner surfaces. The inner surface of the double-layer structure is preferably circular.

In accordance with still another aspect of the present invention, provided is an ADM collagen fiber including, in a cross-sectional view of a heterogeneous acellular dermal matrix (ADM)-derived collagen, a single-layer structure or a double-layer structure with different outer and inner surfaces, wherein the ADM collagen fiber is a crosslinked or non-crosslinked fiber and has a breaking strength of greater than 100 cN.

In accordance with yet another aspect of the present invention, provided is an apparatus for producing an ADM collagen fiber including an extruder configured to extrude an acidic ADM collagen solution into coagulation tanks and equipped with a nozzle having a diameter of 0.1 to 2.5 mm;

the coagulation tanks including guide spools on which filaments are formed, wherein the guide spools serve to guide the formed filaments outward while tensioning the filaments; first rotating spools for guiding the filaments guided outward to a dehydration tank; the dehydration tank including guide spools for guiding the coagulated filaments outward while tensioning the filaments, wherein moisture inside the coagulated filaments is replaced with an organic solvent; a second rotating spool for guiding the filaments guided outward to a winder; and the winder.

Advantageous Effects

The present invention has an effect of providing a method of producing an ADM collagen fiber, the method having excellent economic efficiency and productivity through reduction in production cost and time by preparing a collagen solution raw material having a required concentration by immediately pulverizing ADM collagen shells, being capable of mass production using a continuous process apparatus with a simple structure, having high efficacy due to a wide range of concentrations of available collagen solution raw materials, and being capable of producing collagen fibers having various thicknesses or properties; an ADM collagen fiber produced using the method; and an apparatus for producing the ADM collagen fiber.

DESCRIPTION OF DRAWINGS

FIG. 1 schematically illustrates an apparatus for producing an ADM collagen fiber according to one embodiment of the present invention.

FIG. 2 includes images of the whole and main parts of an apparatus for producing an ADM collagen fiber according to one embodiment of the present invention. Here, arrows indicate enlarged images of the main parts. FIG. 2a is a photograph of a device configured to naturally dry and then wind ADM collagen filaments by controlling the speed of a take-up roller at a distance of about 2 m from a dehydration tank, and FIG. 2b is a photograph of ADM collagen fibers manufactured according to one embodiment of the present invention.

FIG. 3 includes SEM images of the appearances (50×), surfaces (800×), and cross-sections (1,000×) of ADM collagen fibers produced using needles having inner diameters of 21G and 22G, respectively, when performing extrusion in Examples 1 and 2. FIG. 3a is a photograph taken of ADM collagen wet-spun fibers manufactured using needle sizes 21G and 22G placed side by side, and FIGS. 3b and 4c are photographs showing the surface morphology and cross-sectional shape of ADM collagen fibers obtained using needle sizes 21G and 22G, respectively, in a top-down comparison.

FIG. 4 includes graphs showing force-tensile rate percentage according to the size of a needle and the degree of tension when extruding an ADM collagen fiber according to one embodiment of the present invention. FIG. 4a shows undrawn collagen fibers with a needle size of 22G, FIG. 4b shows drawn fibers with a needle size of 22G, and FIG. 4c shows drawn fibers with a needle size of 21G, respectively.

BEST MODE

Hereinafter, a method of producing an ADM collagen fiber, an ADM collagen fiber produced using the method, and an apparatus for producing the ADM collagen fiber according to the present invention will be described in detail.

The conventional wet spinning method of dissolving freeze-dried collagen to produce fibers has disadvantages such as excessive production time and limitation in the usable concentration range of a collagen solution. The present inventors have studied to solve these problems. As a result, the present inventors confirmed that, in the case of a method including a step of extruding an acidic ADM collagen solution into a basic solution to form filaments and a step of performing dehydration and drying using organic solvents such as ethanol, fibers could be easily produced using undried ADM collagen. In addition, simplification of the production process was achieved by significantly increasing the concentration range of a raw material compared to the conventional wet spinning method. Based on these results, the present inventors conducted further studies to complete the present invention.

In the present disclosure, ADM collagen refers to acellular dermis matrix collagen, and collagen recognized as ADM collagen in the technical field to which the present invention pertains, or commercially available or commonly used ADM collagen may be used in the present invention without particular limitation. For example, ADM collagen may be collagen obtained by cells in the dermis after removing the epidermis from the skin tissue of an animal to eliminate immune rejection.

In the present disclosure, collagen in the form of yarn formed during the process from extrusion to winding is referred to as a filament, and collagen after winding is referred to as a collagen fiber. These different terms are used to easily describe the production process of collagen fibers, and these two terms are not mutually exclusive. Filaments and fibers generally recognized in the art to which the present invention pertains may be used without particular limitation.

The method of producing an ADM collagen fiber according to the present invention includes a step of extruding an acidic ADM collagen solution into a basic solution to form filaments. In this case, since the dissolved ADM collagen in an acidic state meets the basic solution and is immediately coagulated, ADM collagen filaments having excellent strength without being dissolved in an organic solvent may be manufactured. In addition, the method of the present invention has excellent economic efficiency and productivity through reduction in production cost and time by preparing a collagen solution raw material having a required concentration by immediately pulverizing ADM collagen shells, is capable of mass production using a continuous process apparatus with a simple structure, has high efficacy due to a wide range of concentrations of available collagen solution raw materials, and is capable of producing collagen fibers having various thicknesses or properties.

Preferably, the method includes a step of performing dehydration by treating the formed filaments with an organic solvent. In this case, economic efficiency may be improved by simplifying the production process of collagen fibers, and mechanical properties such as strength may be excellent.

More preferably, the method includes a step of drying the dehydrated filaments under vacuum or atmospheric pressure. In this case, advantages such as ease of production and economy may be obtained, and deformation over time may be prevented.

More preferably, the method includes a step of winding the dried filaments. In this case, collagen fibers may be easily stored, transported, and used.

The acidic ADM collagen solution preferably includes 1 to 15% by weight of ADM collagen, 0.1 to 20% by weight of an organic acid, and a remainder of water, more preferably 1 to 10% by weight of ADM collagen, 1 to 15% by weight of an organic acid, and a remainder of water, still more preferably 3 to 8% by weight of ADM collagen, 6 to 11% by weight of an organic acid, and a remainder of water, still more preferably 4 to 7% by weight of ADM collagen, 7 to 10% by weight of an organic acid, and a remainder of water. Within this range, economic efficiency and productivity may be excellent, and collagen fibers having excellent physical properties may be mass-produced using a continuous process apparatus having a simple structure.

The organic acid is preferably acetic acid. In this case, an ADM collagen solution may be easily prepared, storage stability may be excellent, and collagen fibers may be easily produced.

The basic solution preferably has a pH of 9 to 12, more preferably 9 to 11, still more preferably 10 to 11. Within this range, collagen fibers may be easily produced, and the produced collagen fibers may have excellent mechanical properties such as strength.

For example, the basic solution may include a base and an organic solvent.

The base is a substance having basic properties when dissolved in an organic solvent. For example, the base may include one or more selected from the group consisting of sodium sulfate, aluminum sulfate, sodium chloride, ammonium sulfate, sodium borate, sodium acetate, calcium hydroxide, sodium hydroxide, and ammonia water, preferably ammonia water. In this case, due to rapid coagulation of ADM collagen, no inorganic salts remain on the produced collagen fibers, thereby achieving excellent physical properties.

In the present disclosure, unless otherwise specified, the organic solvent preferably includes one or more selected from the group consisting of methanol, ethanol, isopropanol, butanol, and ethyl acetate, more preferably methanol, ethanol, or a mixture thereof, still more preferably ethanol. In this case, since fibrosis of ADM collagen is rapidly induced, dehydration and drying of moisture-containing filaments may be easily performed in subsequent steps. In addition, in the produced collagen fibers, filaments do not stick together. In addition, the produced fibers may have excellent physical properties.

Extrusion is preferably performed under conditions of a nozzle diameter of 0.1 to 2.5 mm and a discharge rate of 1 to 30 ml/h per nozzle, more preferably under conditions of a nozzle diameter of 0.3 to 1.0 mm and a discharge rate of 3 to 20 ml/h per nozzle, still more preferably under conditions of a nozzle diameter of 0.4 to 0.8 mm and a discharge rate of 5 to 18 ml/h per nozzle. Within this range, no clogging of a nozzle occurs during operation, productivity may be excellent, and collagen fibers having excellent strength may be produced. As a specific example, extrusion may be performed under conditions of a nozzle diameter of 0.1 to 2.5 mm and a discharge rate of 9 to 13 ml/h.

For example, the number of the nozzles may be one or more, preferably two or more, more preferably three or more. When multi-nozzles composed of several nozzles are applied, productivity may be greatly improved.

The winding step is preferably performed using a winder, preferably a winding machine equipped with a speed-adjustable take-up roller. In this case, by an elongation effect, an ADM collagen fiber having excellent mechanical properties may be produced.

The winding step is preferably performed at a winding rate of 0.1 to 10 m/min. Within this range, by an elongation effect, an ADM collagen fiber having excellent mechanical properties may be produced.

As a specific example, the winding step may be performed at a winding rate of 0.1 to 5 m/min. Within this range, an ADM collagen fiber having a diameter of greater than 500 μm and having excellent mechanical properties may be produced.

As another specific example, the winding step may be performed at a winding rate of 5 to 10 m/min. Within this range, an ADM collagen fiber having a diameter of less than 500 μm and having excellent mechanical properties may be produced.

In addition, the present invention may provide a method of producing an ADM collagen fiber including a neutralization and coagulation step of performing wet spinning of a heterogeneous acellular dermal matrix (ADM)-derived collagen solution and extruding the acidic ADM collagen solution into a basic solution to form filaments; a fiberization step of performing dehydration by treating the filaments formed in the neutralization and coagulation step with an organic solvent; a coagulation step of drying the filaments dehydrated in the fiberization step under vacuum or atmospheric pressure; and a winding step of winding the filaments dried in the coagulation step.

In addition, the present invention may provide a method of producing an ADM collagen fiber including a step of performing wet spinning of a heterogeneous acellular dermal matrix (ADM)-derived collagen solution and extruding the acidic ADM collagen solution into a basic solution having a pH of 9 to 12 to form filaments.

In addition, the present invention may provide a method of producing an ADM collagen fiber including a neutralization and coagulation step of performing wet spinning of a heterogeneous acellular dermal matrix (ADM)-derived collagen solution and extruding the acidic ADM collagen solution into a basic solution having a pH of 9 to 12 to form filaments; a fiberization step of performing dehydration by treating the filaments formed in the neutralization and coagulation step with an organic solvent; a coagulation step of drying the filaments dehydrated in the fiberization step under vacuum or atmospheric pressure; and a winding step of winding the filaments dried in the coagulation step.

In addition, the present invention may provide a method of producing an ADM collagen fiber including a step of performing wet spinning of a heterogeneous acellular dermal matrix (ADM)-derived collagen solution and extruding the acidic ADM collagen solution into a basic solution at a nozzle discharge rate of 9 to 13 ml/h to form filaments.

In addition, the present invention may provide a method of producing an ADM collagen fiber including a neutralization and coagulation step of performing wet spinning of a heterogeneous acellular dermal matrix (ADM)-derived collagen solution and extruding the acidic ADM collagen solution into a basic solution at a nozzle discharge rate of 9 to 13 ml/h to form filaments; a fiberization step of performing dehydration by treating the filaments formed in the neutralization and coagulation step with an organic solvent; a coagulation step of drying the filaments dehydrated in the fiberization step under vacuum or atmospheric pressure; and a winding step of winding the filaments dried in the coagulation step.

In addition, the present invention provides an ADM collagen fiber produced by the method of the present invention.

The ADM collagen fiber of the present invention is produced by the method of the present invention. In this case, since the produced fiber has a uniform shape and excellent physical properties, the reliability of a textile product may be improved.

In a cross-sectional view, the ADM collagen fiber of the present invention preferably has a single-layer structure or a double-layer structure with different outer and inner surfaces. As a preferred example, the inner surface is circular. In this case, due to excellent mechanical properties such as tensile strength, product reliability may be increased. The inner surface is positioned at the center of the fiber like a core, and the outer surface surrounds the inner surface like a shell enclosing the core and is in contact with the outside.

In the present disclosure, the circular shape is not particularly limited when it is a circular shape commonly recognized in the art to which the present invention pertains. For example, the circular shape may include an egg shape, an oval shape, a semicircle shape, and the like, which may be included in the circle category.

The area of the outer surface is preferably smaller than the area of the inner surface.

For example, the fiber may be a non-crosslinked fiber that does not contain a crosslinking agent. In this case, the fiber is not dispersed in water, and the shape thereof may be maintained. Also, the fiber are non-toxic.

As another example, the fiber may be a crosslinked fiber containing a cross-linking agent. In this case, the degree of decomposition may be easily adjusted according to the type and concentration of the crosslinking agent. In addition, strength may be excellent.

The crosslinking agent preferably includes one or more selected from the group consisting of a diepoxy compound, a di(meth)acrylate compound, a diallyl compound, a diisocyanate compound, an imide compound, an acylazide compound, and a divinyl compound, more preferably 1,4-butanediol diglycidyl ether (BDDE), poly(alkylene glycol) diglycidyl ether (PEGDGE), or a mixture thereof. In this case, a crosslinking effect may be sufficiently expressed without degrading the intrinsic properties of the ADM collagen fiber according to the present invention.

For example, the fiber may have a diameter of 10 to 1,000 μm, preferably 20 to 500 μm, more preferably 30 to 200 μm, still more preferably 40 to 150 μm. In this case, the fiber may be applied to a variety of products.

For example, the fiber may have a breaking strength of greater than 100 cN, preferably 100 to 200 CN, more preferably 110 to 150 cN. Within this range, handling of the fiber may be easy, and the fiber may have excellent physical property balance.

In addition, the present invention may provide an ADM collagen fiber produced by the method of the present invention and having a single-layer structure or a double-layer structure with different outer and inner surfaces in a cross-sectional view of a heterogeneous acellular dermal matrix (ADM)-derived collagen, wherein the ADM collagen fiber is a crosslinked or non-crosslinked fiber and has a breaking strength of greater than 100 cN.

Tn apparatus for producing an ADM collagen fiber of the present invention includes an extruder configured to extrude an acidic ADM collagen solution into coagulation tanks and equipped with a nozzle having a diameter of 0.1 to 2.5 mm; the coagulation tanks including guide spools on which filaments are formed, wherein the guide spools serve to guide the formed filaments outward while tensioning the filaments; first rotating spools for guiding the filaments guided outward to a dehydration tank; the dehydration tank including guide spools for guiding the coagulated filaments outward while tensioning the filaments, wherein moisture inside the coagulated filaments is replaced with an organic solvent; a second rotating spool for guiding the filaments guided outward to a winder; and the winder. In this case, ADM collagen shells are immediately pulverized to obtain an acidic ADM collagen solution as a raw material having a required concentration, and the acidic ADM collagen solution is extruded into a coagulation tank containing a basic solution using an extruder to form ADM collagen filaments. Thus, production cost and time may be reduced, thereby increasing economic efficiency and productivity. In addition, mass production is possible using a continuous process apparatus with a simple structure. In addition, due to a wide range of concentrations of available collagen solution raw materials, high efficacy may be achieved, and collagen fibers having various thicknesses or properties may be produced.

For example, the extruder may include one or more nozzles, preferably two or more nozzles, more preferably three or more nozzles. As such, in a multi-nozzle system including several nozzles, productivity may be greatly increased.

The total length of the coagulation tank and the dehydration tank, i.e., the distance that the formed filaments travel, is preferably 2 m or more, more preferably 3 m or more, still more preferably 3 to 4 m. Within this range, since the filaments are sufficiently solidified, the filaments do not break during take-up. In addition, since the collagen fibers do not stick to each other even after roll-up, there are advantages such as ease of use.

The apparatus for producing an ADM collagen fiber preferably includes one or more coagulation tanks between the coagulation tank and the dehydration tank. In this case, the coagulation efficiency of filaments may be excellent.

The dehydration tank and the additional coagulation tanks preferably include a first guide spool taking filaments from the immediately preceding rotating spool inside the tanks and a second guide spool taking the filaments from the first guide spool. In this case, the coagulation efficiency of filaments may be excellent.

The distance between the dehydration tank and a winder, i.e., the distance that the formed filaments travel in air, is preferably 0.5 m or more, more preferably 1 m or more, still more preferably 1 to 3 m, still more preferably 1 to 2 m. Within this range, since the filaments are sufficiently dried, the filaments do not break during take-up. In addition, since the collagen fibers do not stick to each other even after roll-up, there are advantages such as ease of use. Accordingly, it may be important to control the pH of the coagulation tank, the release rate of the collagen solution using a syringe, and the take-up rate.

In the winder, a part of the winder on which the dried filaments are wound is preferably treated with PET or Teflon, more preferably a black Teflon sheet. In this case, it is possible to prevent the collagen fibers from sticking to each other, and there is an advantage that the collagen fibers are clearly visible on the outside, making it easy to check the appearance.

In the present disclosure, PET or Teflon treatment is not particularly limited in the case of PET or Teflon treatment as commonly understood in the art. Preferably, the PET or Teflon treatment means coating a substrate with a PET resin or a Teflon resin or covering a portion with a PET film or a Teflon sheet.

The winder is not particularly limited in the case of a winder generally used in the field of wet spinning fiber technology. Preferably, the winder is a winding machine equipped with a speed-adjustable take-up roller. In this case, productivity may be increased by optimizing drying time.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLES

In the following examples, undried ADM collagen provided from Genewel Co. was used as the ADM collagen, and acetic acid (99.5%), ethanol (94.5%), methanol (99.5%), and ammonia water (28 to 30%) were purchased from Samjeon Chemical.

Example 1

<Preparation of ADM Collagen Solution>

Undried ADM collagen was pulverized using a blender, and 6% by weight of a pulverized solution containing ADM collagen and water was prepared. Then, a 9 M acetic acid solution was added to the pulverized solution to prepare 5.5% by weight of an ADM collagen solution for wet spinning. When the acetic acid solution was added, the solution gradually changed to a transparent gel form and had a high viscosity.

<Production of ADM Collagen Fiber>

FIG. 1 below schematically illustrates an apparatus for producing an ADM collagen fiber according to one embodiment of the present invention, and FIG. 2 below includes images of the whole and main parts of the apparatus for producing an ADM collagen fiber according to one embodiment of the present invention.

Referring to FIG. 1, the apparatus for producing an ADM collagen fiber includes a portion for spinning the prepared ADM collagen solution for wet spinning through an injection needle, a first coagulation tank in which the spun solution is primarily neutralized and coagulated; a second coagulation tank in which gel-type filaments are secondarily condensed and elongated and condensed by tension; and a dehydration tank in which moisture remaining in the filaments is replaced with an organic solvent. The length of each coagulation tank and the dehydration tank was 1 m. Three rotating spools for elongation and one take-up roller for collecting dried collagen filaments were provided outside the coagulation and dehydration tanks. To control elongation speed, the apparatus was configured such that the speed of each spool and the take-up roller could be individually controlled. To move the collagen filaments in a desired direction, guide spools for guiding the elongated collagen filaments were provided in each coagulation tanks and the dehydration tank. In addition, referring to FIG. 2, the apparatus was configured so that ADM collagen filaments could be naturally dried and then wound up by adjusting the speed of the take-up roller at an interval of about 2 m from the dehydration tank.

Referring to FIG. 1, the prepared ADM collagen solution for wet spinning was placed in a plastic syringe and passed through a metal injection needle to form ADM collagen filaments. At this time, the injection angle (the angle at which the fibers exits the needle) was kept as small as possible to prevent the filaments from being damaged. As soon as the filaments emerged from the needle, the filaments were picked up using tweezers and wound on a spool. The undrawn filaments were connected to the take-up roller, and the speed of the roller was adjusted so that the filaments were elongated (For reference, when extra tension is applied to the filaments by the take-up roller at a fixed ejection rate, i.e., at a fixed injection rate, the elongation ratio increases). Use of a needle with too small diameter causes frequent clogging and requires high injection pressure. Thus, a needle with a vertical cross-sectional length (inner diameter) of 21 G was used. At this time, as the syringe, a syringe micro-injection pump system (New Era Pump Systems, Inc. Farmingdale, NY, USA) was used to control volume, time, and speed. At least the tip of the needle was immersed in the first coagulation tank at a predetermined angle (0 to 90 degrees) toward the first coagulation tank. At this time, the ADM collagen solution was released at a rate of 9.0 mL/hour, and the collagen filaments were wound at a rate of 1.4 m/min.

The first and second coagulation tanks were filled with an ethanol solution (basic solution) adjusted to pH 10 with ammonia water, and the dehydration tank was filled with 94.5% by weight of ethanol. As the acid ADM collagen solution passed through the coagulation tanks and the dehydration tank, the acidity of the fibers was adjusted to be neutral.

As soon as the ADM collagen solution extruded and spun through the syringe was exposed to the basic solution contained in the first coagulation tank, the ADM collagen solution was coagulated and transformed into a soft gel-like solid collagen filament capable of supporting the weight thereof up to 3 m in length. As the collagen filaments continuously passed through the second coagulation tank and the dehydration tank, the collagen filaments became harder. The wet spun filaments traveled a total distance of 3 m inside the tanks (1 m movement in each tank) and then were wound onto a take-up roller via a rotating spool installed outside the dehydration tank. At this time, when the acidic ADM collagen solution passed through the coagulation tanks adjusted to pH 10, the acidic ADM collagen solution was neutralized due to a base, and collagen insoluble in ethanol or methanol was precipitated. In addition, moisture in the ADM collagen solution was quickly dissolved into ethanol in the dehydration tank, and fiberization proceeded.

Even after passing through the coagulation tanks and the dehydration tank with a total length of 3 m as described above, collagen filaments immediately discharged from the dehydration tank still contained trace amounts of water and ethanol. Accordingly, after the collagen filaments were moved about 2 m into the air for complete drying, the collagen filaments were wound around the take-up roller. Through this process, collagen fibers were prevented from sticking together after winding. In particular, by attaching a black Teflon sheet to the take-up roller, the amount and state of the collagen fibers could be easily checked while preventing the collagen fibers from sticking to the take-up roller (see FIG. 2B).

Examples 2 to 5

Collagen fibers were produced in the same manner as in Example 1, except that the needle sizes, the release rate of the ADM collagen solution, and the winding rate of the collagen filaments described in Table 1 below were applied.

TABLE 1

| Classification | Example 1 | Example 2 | Example 3 | Example 4 | Example 5 |
|---|---|---|---|---|---|
| Needle size | 21 G | 21 G | 22 G | 22 G | 22 G |
| Release rate of ADM collagen solution (mL/h) | 9.0 | 13.0 | 6.0 | 9.0 | 11.0 |
| Winding rate of collagen filaments (m/min) | 1.4 | 2.0 | 1.1 | 2.0 | 2.4 |

[Test Example] To observe the cross-section of the collagen fibers produced in Examples 1 to 5, a TM 1000 Table Top SEM was used. To check the mechanical properties of the collagen fibers, the breaking strength thereof was measured under conditions of a load cell of 210 cN, a gauge length of 20 mm, and a rate of 2 mm/min using a FAVIMAT and FAVIGRAPH Single-Fiber Tester (Herbert Stein GmbH & Co. KG Dohrweg 65), and the results are shown in FIGS. 3 and 4 below.

FIG. 3 below includes SEM images of the appearances (50×), surfaces (800×), and cross-sections (1,000×) of ADM collagen fibers produced using needles having inner diameters of 21G and 22G, respectively, when performing extrusion in Examples 1 and 2. As shown in FIG. 3, a fiber bundle shape was observed on the surface of the ADM collagen fiber according to the present invention, and a double-layer structure with different external and internal surfaces was observed in the cross-section thereof. More specifically, image (a) shows wet-spun ADM collagen fibers produced using needles having sizes of 21 G and 22 G, respectively. Referring to image (a), the overall fiber shape was observed in both cases. Images (b) and (c) show the surface shapes and the cross-section structures of ADM collagen fibers obtained using needles having sizes of 21 G and 22 G, respectively. Since coagulation occurs from the outside of the ADM collagen solution in the coagulation tank and elongation occurs at the same time, as fiberization progressed from the surface, fibers much thinner than the needle were formed on the outside. Unlike the outside, the inside of the fiber comes into contact with the basic solution of the coagulation tank much more slowly, resulting in a round cross-section. However, the cross section is not a perfect circular structure, but has an intermediate shape in the process of being transformed into a fiber bundle. Such a phenomenon may depend on the concentration, the coagulation rate, the elongation rate, and the like of the ADM collagen solution.

In addition, FIG. 4 below includes graphs showing force-tensile rate percentage according to the size of a needle and the degree of tension when extruding an ADM collagen fiber according to one embodiment of the present invention. In the case of unelongated collagen fibers under the condition of a needle size of 22 G (see (a)), an average breaking strength of about 120 cN was measured. On the other hand, fibers elongated at a needle size of 22 G (see (b)) and fibers elongated at needle size of 21 G (see (c)) exhibited a breaking strength of about 140 cN. It was confirmed that the elongated case had a slightly high breaking strength value. This trend was observed in all examples according to the present invention.

In conclusion, according to the present invention, a solution obtained by pulverizing ADM-treated collagen shells may be used immediately to make a dope solution with a desired collagen concentration. Thus, the concentration of the dope solution may be easily adjusted. Accordingly, compared to the conventional collagen fiber production process, which additionally requires a freeze drying-hydration-grinding process and has an extremely limited collagen concentration range (within 1%), the method of the present invention is very advantageous in terms of time, cost, and productivity. In addition, according to the present invention, by controlling the concentration of the dope solution, controlling the spinning speed (release rate) of the dope solution, controlling residence time in the coagulation tanks, and controlling take-up speed (winding speed), the elongation ratio of the collagen fibers may be easily controlled. In addition, by adjusting the pH of the coagulation tanks, the thickness of the needle, or tensile force, the thickness and shape of the collagen fibers may be easily adjusted. In addition, by applying various nozzle types, the production of collagen fibers may be greatly increased.

The invention claimed is:

1. A method of producing an acellular dermal matrix (ADM) collagen fiber, comprising:
   extruding an acidic ADM collagen solution into a basic solution to form filaments, dehydrating the formed filaments with an organic solvent, drying the dehydrated filaments under vacuum or atmospheric pressure, and winding the dried filaments to produce the ADM collagen fiber, wherein the acidic ADM collagen solution comprises 1 to 15% by weight of an ADM collagen, 0.1 to 20% by weight of an organic acid, and a remainder of water, and wherein the extruding is performed under conditions of a nozzle diameter of 0.1 to 2.5 mm and a discharge rate of 1.0 to 30 ml/h per a nozzle.

2. The method according to claim 1, wherein the organic acid is acetic acid.

3. The method according to claim 1, wherein the basic solution has a pH of 9 to 12.

4. The method according to claim 1, wherein the basic solution comprises a base and an organic solvent.

5. The method according to claim 4, wherein the base is ammonia water.

6. The method according to claim 4, wherein the organic solvent comprises one or more selected from the group consisting of ethanol, methanol, isopropanol, butanol, and ethyl acetate.

7. The method according to claim 1, wherein the organic solvent comprises one or more selected from the group consisting of ethanol, methanol, isopropanol, butanol, and ethyl acetate.

8. The method according to claim 1, wherein, when performing the extrusion, multi-nozzles are applied.

* * * * *